(12) United States Patent
Gopal et al.

(10) Patent No.: US 9,458,121 B2
(45) Date of Patent: Oct. 4, 2016

(54) EPOXIDATION METHODS

(71) Applicant: DOW TECHNOLOGY INVESTMENTS LLC, Midland, MI (US)

(72) Inventors: Srikant Gopal, Pune (IN); Lakshmi N. Vutukuru Murthy, Bangalore (IN); Arun G. Basrur, Pune (IN)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/992,586

(22) Filed: Jan. 11, 2016

(65) Prior Publication Data
US 2016/0122309 A1  May 5, 2016

Related U.S. Application Data

(63) Continuation of application No. 14/114,717, filed as application No. PCT/US2012/039559 on May 25, 2012, now Pat. No. 9,259,726.

(60) Provisional application No. 61/493,553, filed on Jun. 6, 2011.

(51) Int. Cl.
*C07D 301/03* (2006.01)
*C07D 301/04* (2006.01)
(Continued)

(52) U.S. Cl.
CPC ............ *C07D 301/04* (2013.01); *B01J 23/002* (2013.01); *B01J 23/688* (2013.01); *B01J 27/055* (2013.01);
(Continued)

(58) Field of Classification Search
CPC .... C07D 301/04; C07D 31/10; B01J 23/688; B01J 37/0203; B01J 37/024; B01J 23/002; B01J 27/055; B01J 37/0205; B01J 2523/00; B01J 31/2213; C07C 29/106; C07C 41/02; C07C 68/00; C07C 213/02; Y02P 20/52
USPC ...................................................... 549/536
See application file for complete search history.

(56) References Cited

U.S. PATENT DOCUMENTS

| 4,207,210 A | 6/1980 | Kilty |
| 4,530,910 A | 7/1985 | Mross et al. |

(Continued)

FOREIGN PATENT DOCUMENTS

| EP | 0110088 | 6/1984 |
| WO | WO2005023418 | 3/2005 |

(Continued)

OTHER PUBLICATIONS

Jiguang, "Process Technology of Catalyst Preparation", China Petrochemical Press Co., Ltd., Jun. 1, 2004, 6 pp.

*Primary Examiner* — T. Victor Oh
(74) *Attorney, Agent, or Firm* — Joe R. Prieto; KSJLAW, LLC

(57) ABSTRACT

A method for the epoxidation of alkylenes is provided. The method makes use of an epoxidation catalyst comprising a support, silver, manganese and greater than 35 ppm sodium. The catalyst is produced by a method comprising impregnating the support with manganese prior to impregnating the support with sodium and impregnating the support with silver prior to, at the same time as, or after impregnation with manganese. A method for using the alkylene oxides for the production of 1,2-diols, 1,2-carbonates, 1,2-diol ethers is also provided.

20 Claims, 7 Drawing Sheets

(51) Int. Cl.
*B01J 23/00* (2006.01)
*B01J 23/68* (2006.01)
*B01J 27/055* (2006.01)
*B01J 37/02* (2006.01)
*C07D 301/10* (2006.01)
*B01J 31/22* (2006.01)
*C07C 29/10* (2006.01)
*C07C 41/02* (2006.01)
*C07C 68/00* (2006.01)
*C07C 213/02* (2006.01)

(52) U.S. Cl.
CPC ......... *B01J 31/2213* (2013.01); *B01J 37/0203* (2013.01); *B01J 37/024* (2013.01); *C07C 29/106* (2013.01); *C07C 41/02* (2013.01); *C07C 68/00* (2013.01); *C07C 213/02* (2013.01); *C07D 301/10* (2013.01); *B01J 37/0205* (2013.01); *B01J 2523/00* (2013.01); *Y02P 20/52* (2015.11)

(56) References Cited

U.S. PATENT DOCUMENTS

| | | |
|---|---|---|
| 5,112,795 A | 5/1992 | Minahan |
| 5,187,140 A | 2/1993 | Thorsteinson et al. |
| 5,504,053 A | 4/1996 | Chou et al. |
| 8,513,154 B2 | 8/2013 | Allen et al. |
| 2005/0222462 A1 | 10/2005 | Lockemeyer et al. |
| 2006/0258532 A1 | 11/2006 | Thorsteinson et al. |
| 2006/0293180 A1 | 12/2006 | Thorsteinson |
| 2009/0177000 A1 | 7/2009 | Natal et al. |
| 2010/0267975 A1* | 10/2010 | Habenschuss ....... C07D 301/03 549/536 |
| 2011/0082029 A1 | 4/2011 | Thorsteinson et al. |

FOREIGN PATENT DOCUMENTS

| | | |
|---|---|---|
| WO | 2005097318 | 10/2005 |
| WO | 2011145486 | 11/2011 |

\* cited by examiner

EPOXIDATION METHODS

CROSS-REFERENCE TO RELATED APPLICATIONS

This is a continuation application of U.S. patent application Ser. No. 14/114,717, filed Oct. 29, 2013, which, in turn, is a 371 of International Application No. PCT/US2012/039559 filed May 25, 2012, which, in turn, claims the benefit of U.S. provisional patent application Ser. No. 61/493,553, filed Jun. 6, 2011. The contents of the aforementioned applications are incorporated herein by reference in their entirety.

FIELD OF THE INVENTION

Provided herein are methods for the production of epoxidation catalysts. The methods involve multiple impregnations, and the catalysts so produced are expected to exhibit enhanced efficiencies relative to catalysts produced via conventional methods. Epoxidation methods utilizing the catalysts so prepared are also provided.

BACKGROUND

Catalysts are important components of many chemical manufacturing processes, and may typically be used to accelerate the rate of the reaction in question and/or to increase the selectivity or efficiency towards the desired product(s). Utilized in connection with many reactions, catalysts find particular advantageous use in the epoxidation of olefins, a process of significant commercial importance in the commodity chemical business. In epoxidation reactions, a feed containing at least the olefin and oxygen is contacted with a catalyst causing the formation of the corresponding olefin oxide.

One example of an olefin epoxidation of particular commercial importance is the epoxidation of alkylenes, or mixtures of alkylenes, and this epoxidation reaction in particular can rely upon high performing catalysts in order to be commercially viable. Typically, catalysts used in alkylene epoxidation comprise a catalytic species deposited on a suitable support/carrier alone or in combination with one or more promoters.

Those of skill in the art have actively sought improvements in the efficiency and/or activity of epoxidation catalysts for some time, since, on a commercial scale, even slight, e.g., 1%, increases in selectivity can reduce the operating costs associated with the epoxidation processes, substantially.

Research in this area has been wide ranging, and improvements that may provide the catalysts with increased efficiency and/or an extended useful life have been sought in the areas of components of the catalyst, e.g., carriers, promoters, and catalytic species, methods of making the catalyst and even the epoxidation processes themselves. And yet, further improvement would be welcome in the art.

Desirably, methods would be provided that would be capable of producing epoxidation catalysts that exhibit an increase in efficiency relative to conventional catalysts.

SUMMARY OF THE INVENTION

The present invention provides methods for producing epoxidation catalysts that exhibit enhanced efficiencies relative to conventionally produced epoxidation catalysts. More specifically, the present methods provide for the selective impregnation of a catalyst support. It has now been surprisingly discovered that when at least a portion of manganese is impregnated onto a support separate from other alkali metals and/or promoters, the resulting catalyst can exhibit enhanced efficiencies, e.g., of up to 1% greater than catalysts prepared according to conventional methods.

And so, in a first aspect, a method for making an epoxidation catalyst is provided. The epoxidation catalyst comprises a support, at least one catalytic species, manganese and at least one alkali metal and/or promoter. The method comprises impregnating at least a portion of the manganese in an impregnation step separate from the at least one alkali metal and/or promoter. In some embodiments, the manganese may be impregnated onto the support in combination with at least one catalytic species, which in some embodiments may comprise silver.

An epoxidation catalyst prepared according to the method is also provided. The at least one alkali metal and/or promoter may comprise rhenium, sodium, cesium, lithium, sulfate or combinations of these. In certain embodiments, the at least one alkali metal and/or promoter desirably comprises rhenium. In these and other embodiments, the catalytic species may comprise silver.

The epoxidation catalyst, in turn, is expected to exhibit efficiencies of up to 1% greater than epoxidation catalysts produced according to conventional methods. As such, there is also provided a method for the epoxidation of alkylenes. The epoxidation method comprises contacting an oxygen source and an alkylene in the presence of an epoxidation catalyst, wherein the epoxidation catalyst is prepared by impregnating at least a portion of a quantity of manganese in an impregnation step separate from at least one alkali metal and/or promoter.

The increased efficiencies exhibited by the epoxidation catalysts are expected to provide benefit to further downstream products, e.g., in the form of reduced use of materials, reduced time in purifying a final products, etc. There is thus also provided a method for making a 1,2-diol, a 1,2-diol ether, a 1,2-carbonate, or an alkanolamine. The method comprises converting an alkylene oxide into the 1,2-diol, a 1,2-diol ether, a 1,2-carbonate, or alkanolamine. The alkylene oxide is prepared utilizing a catalyst prepared according to the methods described.

DESCRIPTION OF THE DRAWINGS

These and other features, aspects and advantages of the present invention may be further understood and/or illustrated when the following detailed description is considered along with the attached drawings.

DETAILED DESCRIPTION OF THE INVENTION

Figure 1:
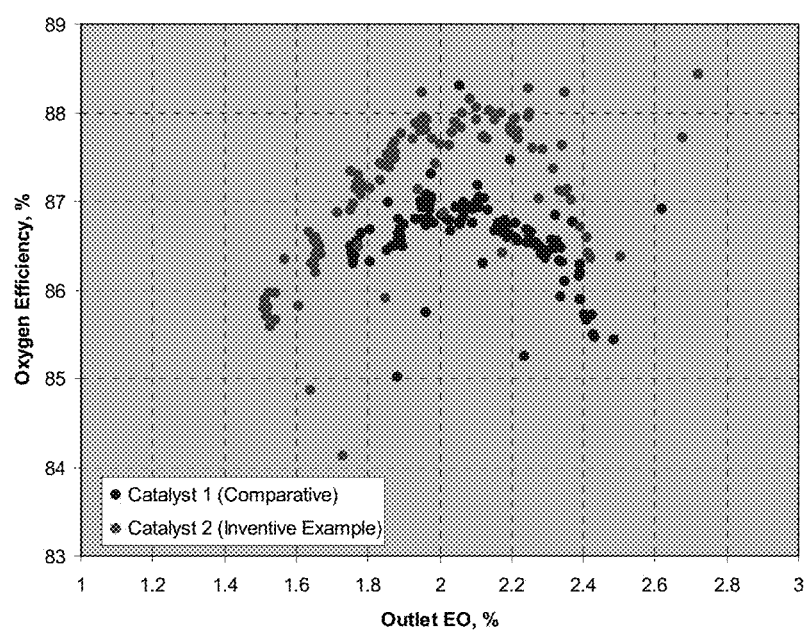
FIG. 1 is a graphical depiction of the % efficiency versus % outlet ethylene oxide concentration of a conventional epoxidation catalyst as well as an epoxidation catalyst produced according to one embodiment of the method.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof; rather, and unless otherwise noted, terms are to be understood according to conventional usage by those of ordinary skill in the relevant art.

Unless defined otherwise, technical and scientific terms used herein have the same meaning as is commonly understood by one of skill in the art to which this invention belongs. The "selectivity" of an epoxidation reaction, which is synonymous with "efficiency," refers to the fraction, expressed as a percentage, of converted or reacted olefin that forms the corresponding olefin oxide product. The terms "efficiency" and "selectivity" are used interchangeably herein. The activity of an epoxidation reaction can be quantified in a number of ways, one being the mole percent of olefin oxide contained in an outlet stream of the reactor relative to that in an inlet stream (the mole percent of olefin oxide in the inlet stream typically, but not necessarily, approaches zero percent) while the reactor temperature is maintained substantially constant; and another being the temperature required to maintain a given rate of olefin oxide production. In many instances, activity is measured over a period of time in terms of the mole percent of olefin oxide produced at a specified constant temperature. Alternatively, activity can be measured as a function of the temperature required to sustain production of a specified constant mole percent of olefin oxide.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

There are provided herein methods of making epoxidation catalysts comprising a support, a catalytic species, manganese and at least one additional alkali metal and/or promoter. More specifically, the methods call for the impregnation of at least a portion of manganese onto the chosen support separately from the at least one additional alkali metal and/or promoter, and in some embodiments, separate from the catalytic species.

It has now been surprisingly discovered that by employing the described methods, catalysts can be obtained that exhibit selectivities of up to 1% higher than catalysts prepared by conventional methods. That is, so long as at least a portion of manganese to be included in the catalyst is impregnated separately from any other alkali metals and/or promoters to be included in the catalyst, the beneficial effects provided by the present methods are expected to be seen in the catalysts prepared thereby, regardless of the other alkali metals and/or promoters utilized.

The manganese may be provided in the form of an anionic promoter, e.g., in the form of an oxyanion (manganates), or a mixed metal oxyanion, including polyoxyanion structures. It is well recognized that many anionic promoters have complex chemistries and may exist in one or more forms, and any of these are acceptable for use as the source of manganese in the present methods. Furthermore, it is also known that oxyanions or precursors to oxyanions may be used in the solutions for impregnating the carrier, and that, during the conditions of preparation of the catalyst and/or during its use, the particular manganese oxyanion or precursor initially present may be converted to another form. The invention is not intended to be limited by the exact manganese species that may ultimately exist on the catalyst during use. And so, exemplary manganese components include, but are not limited to manganese acetate, manganese ammonium sulfate, manganese citrate, manganese dithionate, manganese oxalate, manganous nitrate, manganous sulfate and manganate anion, for example, permanganate anion, and mixtures thereof. To stabilize the manganese component in certain impregnating solutions, a chelating compound, such as ethylenediaminetetraacetic acid (EDTA) may be added to the impregnating solution in some embodiments.

In addition to manganese, catalysts prepared according to the present invention desirably comprise at least one other alkali metal and/or promoter. As is known to those skilled in the art, there are a variety of known promoters, or materials which, when present in combination with particular catalytic materials, e.g., silver, benefit one or more aspects of catalyst performance or otherwise act to promote the catalyst's ability to make a desired product, e.g., ethylene oxide or propylene oxide. More specifically, and while such promoters in themselves are generally not considered catalytic materials, they typically may contribute to one or more beneficial effects of the catalysts' performance, for example enhancing the rate, or amount, of production of the desired product, reducing the temperature required to achieve a suitable rate of reaction, reducing the rates or amounts of undesired reactions, etc. Furthermore, and as those of ordinary skill in the art are aware, a material which can act as a promoter of a desired reaction can be an inhibitor of another reaction. For purposes of the present invention, a promoter is a material which has an effect on the overall reaction that is favorable to the efficient production of the desired product, whether or not it may also inhibit any competing reactions that may simultaneously occur.

Exemplary alkali metals and/or promoters include, but are not limited to, the group of Group IA metals, Group IIA metals, rhenium, molybdenum, tungsten, lithium, sulfur, potassium, rubidium, cesium, chromium, titanium, hafnium, zirconium, vanadium, thallium, thorium, tantalum, niobium, calcium, barium, gallium and germanium and mixtures thereof. Preferably the further metal is selected from the Group IA metals such as lithium, potassium, sodium, rubidium and cesium and/or from the Group IIA metals such as calcium and barium. Most preferably it is lithium, potassium, sodium and/or cesium.

Rhenium, molybdenum or tungsten may suitably be provided as oxyanions, for example, as perrhenate, molybdate, or tungstate, in salt or acid form. Examples of promoters, their characteristics, and methods for incorporating the promoters as part of the catalyst are described in Thorsteinson et al., U.S. Pat. No. 5,187,140, particularly at columns 11 through 15, Liu, et al., U.S. Pat. No. 6,511,938, Chou et al., U.S. Pat. No. 5,504,053, Soo, et al., U.S. Pat. No. 5,102,848, Bhasin, et al., U.S. Pat. Nos. 4,916,243, 4,908,343, and 5,059,481, and Lauritzen, U.S. Pat. Nos. 4,761,394, 4,766, 105, 4,808,738, 4,820,675, and 4,833,261.

In some embodiments, the catalysts prepared by the present method may comprise rhenium and one or more additional alkali metals and/or promoters. Rhenium-promoted supported silver containing catalysts are known from U.S. Pat. Nos. 4,761,394 and 4,766,105. In such embodiments, the rhenium component can be provided in various forms, for example, as the metal, as a covalent compound, as a cation or as an anion. The rhenium species that provides the enhanced efficiency and/or activity is not certain and may be the component added or that generated either during preparation of the catalyst or during use as a catalyst.

Examples of rhenium compounds include the rhenium salts such as rhenium halides, the rhenium oxyhalides, the rhenates, the perrhenates, the oxides and the acids of rhenium. However, the alkali metal perrhenates, ammonium perrhenate, alkaline earth metal perrhenates, silver perrhenates, other perrhenates and rhenium heptoxide may also be used. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, that is, $ReO_4$. Similar chemistries can be exhibited by other metals such as molybdenum and tungsten.

The manganese and any other desired promoters and/or alkali metals included in the catalyst to be subjected to the present method, are desirably provided in a promoting or effective, amount, and such amounts are readily determined by those of ordinary skill in the art. A "promoting amount" of a certain promoter refers to an amount of that promoter that works effectively to provide an improvement in one or more of the properties of a catalyst comprising the promoter relative to a catalyst not comprising said promoter. Examples of catalytic properties include, inter alia, operability (resistance to run-away), selectivity, activity, conversion, stability and yield. The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

The amount of manganese promoter may vary widely, or from 0.0005 to 2 weight percent, based upon the total weight of the catalyst, and may depend to some extent on the surface area of the carrier. For example, when the carrier surface area is in the range of from 1.0 m2/g to 1.3 m2/g, the manganese component may be provided in an amount of at least 5 ppm, or at least 10 ppm, or from 10 ppm to 1000 ppm, or between 20 ppm and 300 ppm by weight, based upon the total weight of the catalyst. In some embodiments, the amount of manganese added may be at least 1.5 micromoles per gram of catalyst.

Exemplary suitable amounts of rhenium are expected to range from 0.0001 weight percent (1 ppmw) to 2 weight percent (20,000 ppmw), preferably from 0.0005 weight percent (5 ppmw) to 0.5 weight percent (5000 ppmw) based on the total weight of the catalyst. Exemplary suitable amounts of cesium are expected to range from 0.005 weight percent to 0.30 weight percent, or from 0.005 weight percent to 0.15 weight percent, based upon the total weight of the catalyst. Stated another way, suitable amounts of cesium can range from greater than 200 ppm to 1200 ppm, based on the weight of the catalyst. Exemplary suitable amounts of sulfur are expected to range from 0.0025 weight percent to 0.15 weight percent, or from 0.001 weight percent to 0.075 weight percent, based upon the total weight of the catalyst.

Generally, such catalysts are supported catalysts, and may comprise any of the large number of known porous refractory structure or support materials, so long as whatever the porous refractory material chosen, it is relatively inert in the presence of the chemicals and processing conditions employed in the application in which the shaped porous body will be utilized. It may also be important that the support materials, and thus catalysts based upon the same, be able to withstand fairly large temperature and pressure fluctuations within the reactor.

There are many well-known methods of preparing supports suitable for use in alkylene oxide catalysts. Some of such methods are described in, for example, U.S. Pat. Nos. 4,379,134; 4,806,518; 5,063,195; 5,384,302; 6,831,037 and the like. For example, an alpha-alumina support of at least 95% purity can be prepared by compounding (mixing) the raw materials, extrusion, drying and a high temperature calcination. In this case, the starting raw materials usually include one or more alpha-alumina powder(s) with different properties, a clay-type material which may be added as binder to provide physical strength, and a burnout material (usually an organic compound) used in the mix to provide desired porosity and/or pore size distribution after its removal during the calcination step. The levels of impurities in the finished support are determined by the purity of the raw materials used, and their degree of volatilization during the calcination step. Common impurities may include silica, alkali and alkaline earth metal oxides and trace amounts of metal and/or non-metal-containing additives.

Another method for preparing a support having particularly suitable properties for alkylene oxide catalyst usage comprises optionally mixing zirconium silicate with boehmite alumina (AlOOH) and/or gamma-alumina, peptizing the aluminas with a mixture containing an acidic component and halide anions (preferably fluoride anions) to provide peptized halogenated alumina, forming (for example, by extruding or pressing) the peptized halogenated alumina to provide formed peptized halogenated alumina, drying the formed peptized halogenated alumina to provide dried formed alumina, and calcining the dried formed alumina to provide pills of optionally modified alpha-alumina support.

In one embodiment, the support material comprises at least 80 weight percent alpha-alumina and comprises less than 30 parts per million acid-leachable alkali metals by weight, the weight percent of the alpha-alumina and the concentration of the acid-leachable alkali metals being calculated on the weight of the support, where the acid-leachable alkali metals are selected from lithium, sodium, potassium, and mixtures thereof.

Preparation of the support material may further comprise any other component, in any amounts, necessary or desired for processing, such as, e.g., water, acid, binders, lubricants dispersants, pore formers, dopants, modifiers, etc, such as those described in *Introduction to the Principles of Ceramic Processing*, J. Reed, Wiley Interscience, (1988).

The support material(s) will desirably be porous and have measured surface areas of at least 0.5 $m^2/g$ (more preferably from 0.7 $m^2/g$ to 10 $m^2/g$), measured pore volumes of at least 0.3 cc/g (more preferably from 0.4 cc/g to 2.0 cc/g), and median pore diameters from 1 to 50 microns.

"Surface area", as used herein, refers to the surface area as measured by the BET (Brunauer, Emmett and Teller) method by nitrogen as described in the Journal of the American Chemical Society 60 (1938) pp. 309-316. "Total pore volume" means pore volume of the support material and is typically determined by mercury porosimetry. "Porosity" is the proportion of the non-solid volume to the total volume of material. Total pore volume as measured by mercury porosimetry or water absorption may be used to estimate porosity by those of skill in the art. "Median pore diameter" means the pore diameter corresponding to the point in the pore size distribution at which half of the total pore volume of the shaped porous body has been measured.

The support materials/catalysts can be of any desired, suitable shape. Conventional commercial fixed bed ethylene oxide reactors are typically in the form of a plurality of parallel elongated tubes (in a suitable shell) having an outer diameter of from 2 to 7 cm and a length of from 4 to 14 m. For use in such fixed bed reactors, the support materials/catalysts will desirably be formed into a rounded shape, such as, for example, spheres, pellets, rings, tablets, and the like, having diameters from 0.1 inch (0.25 cm) to 0.8 inch (2 cm).

In addition to the support material, manganese and at least one additional alkali metal and/or promoters, the epoxidation catalysts include at least one catalytic species deposited thereupon. Non-limiting examples of catalytic species that may advantageously be supported by the support material include metals, solid state compounds, molecular catalysts, enzymes and combinations of these. Typically, catalysts useful for the epoxidation of ethylene utilize silver as the catalytic species, and the same is preferred in some embodiments of the invention.

Any amount of silver capable of catalyzing the direct oxidation of, e.g., ethylene, with oxygen or an oxygen-containing gas to the corresponding alkylene oxide, may be used. Typically, the support material will be impregnated with one or more silver compound solutions sufficient to allow the silver to be provided on the support material in an amount greater than 5 percent, greater than 10 percent, greater than 15 percent, greater than 20 percent, greater than 25 percent, preferably, greater than 27 percent, and more preferably, greater than 30 percent by weight, based on the weight of the catalyst. Although the amount of silver utilized is not particularly limited, the amount of silver provided in connection with the support material may usually be less than 70 percent, and more preferably, less than 50 percent by weight, based on the weight of the catalysts.

In terms of density, the catalytic species, e.g., silver, relative to the surface area of the support material may be present in amounts up to at least 0.07 $g/m^2$, or up to 0.2 $g/m^2$, or even up to 0.3 $g/m^2$ or more.

Although silver particle size in the finished catalysts is important, the range is not narrow. A suitable silver particle size can be in the range of from 10 angstroms to 10,000 angstroms in diameter. A preferred silver particle size ranges from greater than 100 angstroms to less than 5,000 angstroms in diameter. It is desirable that the silver be relatively uniformly dispersed within, throughout, and/or on the shaped porous body.

The impregnation solutions may comprise catalytic species, e.g., silver, or may comprise only the promoter(s) desirably impregnated onto the carrier. For purposes of the present invention, all that is required is that in at least one impregnation step, manganese is impregnated separately from any other desired/required alkali metal(s) and/or promoter(s). If silver is to be included in the impregnating solution with the manganese, the silver may be provided in any solvent or complexing/solubilizing agent known in the art. Examples of these include, but are not limited to, lactic acid; ammonia; alcohols, such as ethylene glycol; and amines and mixtures of amines. One particular example of an impregnating solution might comprise silver oxide dissolved in a solution of oxalic acid and ethylenediamine to approximately 30 percent silver by weight, and the desired amount of manganese. In other embodiments, manganese may be dissolved in the desired amount in the desired solvent alone.

The sequence of impregnating the support with the catalytic species and the at least one other alkali metal and/or promoter may vary, so long as that in at least one impregnation step, an amount of manganese is deposited separately from any other alkali metals or promoters desirably deposited onto the support. In some embodiments, further amounts of manganese may desirably be deposited on the support in combination with amounts of the catalytic species and/or other alkali metals or promoters desirably deposited on the support.

For example, the silver may be deposited first separately, followed by an impregnation of manganese alone, followed by coincidental or sequential impregnations of any other desired alkali metals and/or promoters. Or, an amount of the catalytic species and an amount of manganese may be deposited in one impregnation and a further amount of the catalytic species and manganese may be deposited in a further impregnation step along with one or more alkali metals and/or promoters, etc. Or, an amount of manganese may be impregnated onto the support, followed by an impregnation of the desired catalytic species and at least one alkali metal and/or promoter. In other embodiments, the steps may be reversed, i.e., the support may be impregnated with a solution comprising the at least one alkali metal and/or promoter and/or catalytic species and then be impregnated with the solution comprising manganese. The impregnating solution comprising manganese may or may not comprise an amount of the catalytic species. And, the impregnation of the catalytic species and other alkali metals and/or promoters may occur coincidentally or sequentially. If two or more impregnations are employed, the impregnated carrier is typically dried, or calcined and/or roasted between each successive impregnation to ensure deposition of the metals onto the support.

In one embodiment, a two-step impregnation is used. In a first step, the support is impregnated with a solution comprising a solvent or solubilizing agent, a silver solution and manganese. Thereafter, the impregnated carrier is calcined under air (or other atmospheres, such as in nitrogen, helium and/or steam) at a temperature ranging from 200° C. to 600° C. and at atmospheric pressure for a time ranging from 0.01 hours to 12 hours. Optionally, the impregnated support may be dried in an oven to remove the solvent prior to calcination. In a second step, the impregnated support is impregnated with a solution containing additional silver compound and promoting amounts of at least one alkali metal and/or promoter. The support is then again calcined or roasted under air at a temperature ranging from 200° C. to 600° C. and at atmospheric pressure for a time ranging from 0.01 hours to 12 hours.

Catalysts prepared according to the methods described herein are expected to exhibit efficiencies of up to 1% greater than catalysts produced according to conventional methods when used in epoxidation methods. Such methods generally involve exposing the catalyst to a feed stream comprising the desired alkylene, an oxygen source, and typically, one or more gas phase promoters.

Gas phase epoxidation reaction promoters are thought to be capable of increasing the efficiency and/or activity of epoxidation catalysts by either increasing the rate towards the formation of the desired alkylene oxide and/or suppressing the oxidation of alkylene or alkylene oxide to form carbon dioxide and water, relative to the formation of the desired alkylene oxide. Many such promoters are known, and any of these may be used in the method of the present invention. Typically, gas phase promoters useful in epoxidation reactions include organic compounds, and in particular include organic halides, e.g., bromides or chlorides. "Promoters" are sometimes referred to as "inhibitors" or "moderators."

Of these, chloro- and bromohydrocarbons are particularly preferred. Examples of these include, but are not limited to, methyl chloride, ethyl chloride, ethylene dichloride, ethylene dibromide, vinyl chloride, or any combination of these. Particularly preferred gas phase epoxidation reaction promoters for use in the present method are ethyl chloride and ethylene dichloride.

Using chlorohydrocarbon gas phase promoters as an example, it is believed that the ability of the promoter to enhance the efficiency and/or activity for the desired alkylene oxide depends on the extent to which the gas phase promoter chlorinates the surface of the catalyst, for example, by depositing particular chlorine species such as atomic chlorine or chloride ions on the catalyst or in the gas phase above the catalyst. However, hydrocarbons lacking chlorine atoms are believed to strip chlorides from the catalyst, and therefore, detract from the overall enhancement provided by the gas phase promoter. Discussions of this phenomenon may be found in Berty, "Inhibitor Action of Chlorinated Hydrocarbons in the Oxidation of Ethylene to Ethylene Oxide," Chemical Engineering Communications, Vol. 82 (1989) at 229-232 and Berty, "Ethylene Oxide Synthesis," Applied Industrial Catalysis, Vol. I (1983) at 207-238. Paraffinic compounds, such as ethane or propane, are believed to be especially effective at stripping chlorides from the catalyst. However, olefins, such as ethylene and propylene, are also believed to act to strip chlorides from the catalyst. Some of these hydrocarbons may also be introduced as impurities in the ethylene feed or may be present for other reasons (such as the use of a recycle stream). Typically, the preferred concentration of ethane in the feed, when present, is from 0 to 2 mole percent. Given the competing effects of the gas phase promoter and the non-halogenated, non-promoting hydrocarbons in the reactor feed stream, it is convenient to define an "overall halogenating effectiveness value," which in the case of organic chlorides is an "overall chloriding effectiveness value" that represents the net effect of the promoting and non-promoting gas phase species in halogenating (or chloriding) the catalyst. In the case of organic chloride gas-phase promoters, the overall chloriding effectiveness can be defined as the dimensionless quantity Z* and represented by the following formula:

$$Z^* = \frac{\text{ethyl chloride equivalent (ppmv)}}{\text{ethane equivalent (mole percent)}} \quad (1)$$

wherein the ethyl chloride equivalent is the concentration in ppmv of ethyl chloride that provides substantially the same catalyst chloriding effectiveness of the organic chlorides present in the reactor feed stream at the concentrations of the organic chlorides in the feed stream; and the ethane equivalent is the concentration of ethane in mole percent that provides substantially the same catalyst dechloriding effectiveness of the non-chloride containing hydrocarbons in the feed stream at the concentrations of the non-chloride containing hydrocarbons in the feed stream.

If ethyl chloride is the only gaseous chloride-containing promoter present in the reactor feed stream, the ethyl chloride equivalent is the ethyl chloride concentration in ppmv. If another chlorine-containing promoter (specifically vinyl chloride, methyl chloride or ethylene dichloride) is used alone or in conjunction with ethyl chloride, the ethyl chloride equivalent is the sum of the concentration of ethyl chloride in ppmv and the concentrations of the other gaseous chloride-containing promoters (corrected for their effectiveness as a promoter as compared to ethyl chloride). The relative effectiveness of a non-ethyl chloride promoter can be measured experimentally by replacing ethyl chloride with the other promoter and determining the concentration needed to obtain the same level of catalyst performance provided by ethyl chloride. As a way of further illustration, if the required concentration of ethylene dichloride at the reactor inlet is 0.5 ppmv to realize equivalent effectiveness in terms of catalyst performance provided by 1 ppmv ethyl chloride, then the ethyl chloride equivalent for 1 ppmv ethylene dichloride would be 2 ppmv ethyl chloride. For a hypothetical feed having of 1 ppmv ethylene dichloride and 1 ppmv ethyl chloride, the ethyl chloride equivalent in the numerator of Z* would then be 3 ppmv. As a further example, it has been found for certain catalysts that methyl chloride has 10 times less the chloriding effectiveness of ethyl chloride. Therefore, for such catalysts, the ethyl chloride equivalent for a given concentration of methyl chloride in ppmv is 0.1×(methyl chloride concentration in ppmv).

The ethane equivalent is the concentration of ethane in mole percent in the reactor feed stream plus the concentrations of the other hydrocarbons effective in removing chloride from the catalysts, corrected for their effectiveness for dechlorination relative to ethane. The relative effectiveness of ethylene and ethane can be measured experimentally by determining the inlet ethyl chloride equivalent concentration that provides the same level of catalyst performance for a feed comprising both ethylene and ethane as compared to the same feed with the same ethylene concentration but a specific ethyl chloride equivalent concentration and no ethane.

As a way of further illustration, if with a feed composition comprising an ethylene concentration of 30.0 mole percent and an ethane concentration of 0.30 mole percent, a level of 6.0 ppm ethyl chloride equivalents is found to provide the same level of catalyst performance as 3.0 ppm ethyl chloride equivalents with a similar feed composition but lacking ethane, then the ethane equivalent for 30.0 mole percent ethylene would be 0.30 mole percent. For an inlet reactor feed having 30.0 mole percent ethylene and 0.3 mole percent ethane, the ethane equivalent will then be 0.6 mole percent. As another illustration, it has been found that, for certain catalysts, methane has 500 times less the dechloriding effectiveness of ethane. Thus, for such catalysts, the ethane equivalent for methane is 0.002×(methane concentration in mole %). For a typical inlet reactor feed having 30.0 mole percent ethylene and 0.1 mole percent ethane, the ethane equivalent then will be 0.4 mole percent.

The relative effectiveness of hydrocarbons other than ethane and ethylene can be measured experimentally by determining the inlet ethyl chloride equivalent concentrations required to achieve the same catalyst performance for a feed comprising the hydrocarbon of interest at its feed concentration at two different feed ethane concentrations. If a hydrocarbon compound is found to have a very small dechloriding effect and is also present in low concentrations, then its contribution to the ethane equivalent concentration in the Z* calculation will be negligible.

Thus, given the foregoing relationships, in the case where the reactor feed stream includes ethylene, ethyl chloride, ethylene dichloride, vinyl chloride, and ethane, the overall chloriding effectiveness value of the process can be defined as follows:

$$Z^* = \frac{(ECL + 2^*EDC + VCL)}{(C_2H_6 + 0.01^*C_2H_4)} \quad (2)$$

wherein ECL, EDC, and VCL are the concentrations in ppmv of ethyl chloride ($C_2H_5Cl$), ethylene dichloride (Cl—$CH_2$—$CH_2$—Cl), and vinyl chloride ($H_2C=CH$—Cl), respectively, in the reactor feed stream. $C_2H_6$ and $C_2H_4$ are the concentrations in mole percent of ethane and ethylene, respectively, in the reactor feed stream.

Those of skill in the art will recognize that although a single chlorohydrocarbon promoter may be utilized in some embodiments of the invention, upon contact with the catalyst under epoxidation reaction conditions, a variety of compounds may be formed and thus are present in the process. As such, it is to be understood, that even if one, or a certain, gas-phase promoter is initially utilized in the present method, the scope of the claims is considered to include not only the introduced promoter(s), but any or all of its/their reaction products that may be formed during application of the method.

One class of catalysts that may find particular benefit from application of the present invention includes those useful for the epoxidation of olefins, and in particular, for the epoxidation of alkylenes, or mixtures of alkylenes. Many references describe these reactions, representative examples of these being Liu et al., U.S. Pat. No. 6,511,938 and Bhasin, U.S. Pat. No. 5,057,481, as well as the Kirk-Othmer's Encyclopedia of Chemical Technology, 4th Ed. (1994) Volume 9, pages 915-959. Although the invention is not so limited, for purposes of simplicity and illustration, application of the present method is further described in terms of and with reference to catalysts useful for the epoxidation of ethylene.

It has now been surprisingly discovered that epoxidation catalysts prepared according to the methods described herein can exhibit efficiencies up to at least 1% greater than epoxidation catalysts prepared according to conventional processes. The present methods thus provide significant cost and time savings. Further cost savings can be realized in the form of raw material savings provided by the increased efficiency of catalysts produced according to the methods.

As such, the present invention also provides a method for the epoxidation of alkylenes. Those of ordinary skill in the chemical engineering art are familiar with such processes. One exemplary process is described in Kirk-Othmer's Encyclopedia of Chemical Technology, $4^{th}$ ed., Vol. 9, 1994, pp. 925-939.

Generally speaking then, the epoxidation reaction may take place in any suitable reactor, for example, fixed bed reactors, continuous stirred tank reactors (CSTR), and fluid bed reactors, a wide variety of which are well known to those skilled in the art and need not be described in detail herein. The desirability of recycling unreacted feed, employing a single-pass system, or using successive reactions to increase ethylene conversion by employing reactors in series arrangement can also be readily determined by those skilled in the art. The particular mode of operation selected is usually dictated by process economics.

The epoxidation reaction is generally exothermic. Thus, a coolant system (e.g., a cooling jacket or a hydraulic circuit with a coolant fluid such as a heat transfer fluid or boiling water) may be provided to regulate the temperature of the reactors. The heat transfer fluid can be any of several well-known heat transfer fluids, such as tetralin (1,2,3,4-Tetrahydronaphthalene). In reactors cooled with boiling water, the coolant is introduced to the cooling side of the reactor, most commonly the shell side, as liquid water. As it flows through the cooling side, the water removes heat from the process side, and some of the water is vaporized to steam. The coolant exits the cooling side of the reactor as a mixture of water and steam. The steam exiting the reactor is condensed by removing heat from it, and is recycled back to the inlet of the coolant side.

The temperature of the coolant in the reactor is determined by the boiling point of the water, which in turn is determined by the pressure under which it operates. The pressure is controlled by means of a vent valve which vents off some pressure from the steam-water mixture exiting the cooling side of the reactor. Typically, a closed-loop controller is used to regulate the coolant temperature by automatically adjusting the vent valve to maintain the pressure necessary to maintain the desired temperature.

Conversion of olefin (alkylene), preferably ethylene, to olefin oxide, preferably ethylene oxide, can be carried out, for example, by continuously introducing a feed stream containing alkylene (e.g., ethylene) and oxygen or an oxygen-containing gas and a gas phase promoter at parts per million level to a catalyst-containing reactor at a temperature of from 200° C. to 300° C., and a pressure which may vary between 5 atmospheres (506 kPa) and 30 atmospheres (3.0 MPa), depending upon the mass velocity and productivity desired. Oxygen may be supplied to the reaction in an oxygen-containing stream, such as, air or as pure oxygen, or as oxygen-enriched air. The resulting alkylene oxide, preferably, ethylene oxide, is separated and recovered from the reaction products using conventional methods.

Any alkylene can be utilized in the process, and examples of those that may desirably be epoxidized include, but are not limited to, 1,9-decadiene, 1,3-butadiene, 2-butene, isobutene, 1-butene, propylene, ethylene, or combinations of these. Preferably, the alkylene comprises ethylene.

Typically, epoxidation reactions may desirably be carried out in the gas phase, with a feed comprising the desired alkylene and oxygen being caused to come in contact with an epoxidation catalyst. Oftentimes, the catalyst is present as a solid material, and more particularly, may be present as a packed bed within the desired reactor. The quantity of catalyst in the packed bed may be at least 10 kg, or at least 20 kg, or from $10^2$ to $10^2$ kg or from $10^3$ to $10^6$ kg.

Many epoxidation reactions are carried out as continuous processes, and the same is contemplated here. In such processes, the desired reactor may typically be equipped with heat exchange equipment to control the temperature of the process, within the reactor and/or the catalyst bed.

The feed may additionally comprise one or more optional components, including, for example, carbon dioxide, inert gases, saturated hydrocarbons and the like. Carbon dioxide may, in particular, be expected to be present when recycling of the feed is conducted, since carbon dioxide is a by-product of many epoxidation processes. In these embodiments, at least part of the carbon dioxide in the recycled gas is removed via conventional ways such as those described in Kirk-Othmer's Encyclopedia of Chemical Technology, 4$^{th}$ Ed. (1994) Volume 9, pages 915-959, since carbon dioxide has an adverse effect on catalyst performance, especially activity. The inert gas may comprise nitrogen, argon, or mixtures thereof. Saturated hydrocarbons such as methane may be utilized to control heat within the reactor and allow a higher oxygen concentration in the feed.

In one embodiment, the process for the oxidation of an alkylene comprises contacting a reaction mixture feed comprising an alkene, oxygen, and carbon dioxide, with a catalyst prepared according to the provided methods comprising a carrier and, deposited on the carrier, silver, manganese and at least one additional promoter and/or alkali metal; wherein the carbon dioxide is present in the reactor mixture in a quantity of at most 3 mole percent based on the total reaction mixture; and the at least one additional promoter and/or alkali metal comprises sodium, cesium, lithium, sulfate and mixtures thereof.

During operation, the pressure at the inlet of the epoxidation reactor may typically be less than 4000 kPa, or less than 3500 kPa, or preferably will be less than 2500 kPa absolute, and in most instances will be at least 1000 kPa absolute. The gas hourly space velocity, ("GHSV") is the unit volume of gas at standard state temperature and pressure (0° C., 1 atm) passing over one unit volume of packed catalyst bed per hour. Preferably in those embodiments wherein the epoxidation reaction is carried out in the gas phase, over a packed catalyst bed, the GHSV in the start-up phase is desirably from 2000 to 10000 per hour.

During operation, the feed composition may remain substantially unchanged. More particularly, the reactor inlet oxygen concentration may desirably remain substantially unchanged, e.g., at 8 mole-%, the reactor inlet alkylene concentration may desirably remain substantially unchanged, e.g., at 30 mole-%, the inlet carbon dioxide concentration may also remain substantially unchanged, e.g., at 3 mole-% and the overall catalyst chloriding effectiveness value may remain substantially unchanged, e.g., at 3 when expressed as $Z^*$.

As those of skill in the art will readily appreciate, other parameters of the epoxidation process may also be adjusted in order to achieve a desired rate of alkylene oxide production during the periods at elevated and/or reduced temperature. For example, the reactor pressure and/or the space velocity may be changed along with or instead of the inlet feed composition in order to achieve a particular production rate at a particular operating temperature.

Or, in some embodiments, the feed composition may be altered during the epoxidation process. If desired, the reactor inlet oxygen concentration may be decreased, e.g., by at least 1 mole-%, or by 2 mole-% or even 3 mole-%, so long as safe operating conditions and desired alkylene oxide production are maintained. The inlet carbon dioxide concentration may advantageously be increased, e.g., by at least 0.5 mole-%, or 1 mole-%, the amount of such increase in certain cases being limited by the design of the epoxidation process. The overall catalyst chloriding effectiveness value may advantageously be decreased, e.g., by at least 0.5 or even 1.0 or more $Z^*$ units, the amount of such decrease being limited in certain cases by the amount of recycle in the process design. The inlet alkylene concentration may be substantially maintained, or, may be decreased by 5 or 10 or even 15 mole-%, concurrent with the period(s) at elevated temperature. In any case, the adjustments or combinations thereof will desirably provide the desired level of alkylene oxide.

The alkylene oxide produced by the present epoxidation process may typically be processed to provide further downstream products, such as, for example, 1,2-diols, 1,2-diol ethers, 1,2-carbonates, and alkanolamines. Since the present invention provides epoxidation catalysts that exhibit efficiencies of at least 1% greater than efficiencies exhibited by catalysts produced according to conventional methods, it is contemplated that the improvements provided will carry forward to provide improvements to these downstream processes and/or products. Improved methods for the production of 1,2-diols, 1,2-carbonates, 1,2-diol ethers and alkanolamines are thus also provided herein.

The conversion of alkylene oxides into 1,2-diols or 1,2-diol ethers may comprise, for example, reacting the desired alkylene oxide with water, suitably in the presence of an acidic or basic catalyst. For example, for preferential production of the 1,2-diol over the 1,2-diol ether, the alkylene oxide may be reacted with a tenfold molar excess of water, in a liquid phase reaction in the presence of an acid catalyst, e.g., 0.5-1.0 wt % sulfuric acid, based on the total reaction mixture, at 50-70C at 1 bar absolute, or in a gas phase reaction, at 130-240° C. and 20-40 bar absolute, preferably in the absence of a catalyst. If the proportion of water is lowered, the proportion of the 1,2-diol ethers in the reaction mixture will be increased. The 1-2, diol ethers thus produced may comprise di-ethers, tri-ethers, tetra-ethers or other multi-ethers. Alternative 1,2-diol ethers may be prepared by converting the alkylene oxide with an alcohol, such as methanol or ethanol, or by replacing at least a portion of the water with the alcohol. The resulting 1,2-diols and diol ethers may be utilized in a wide variety of end-use applications in the food, beverage, tobacco, cosmetic, thermoplastic polymer, curable resin system, detergent, heat transfer system, etc., industries.

The conversion of alkylene oxides produced using catalysts produced according to the present invention into alkanolamines may comprise, for example, reacting the alkylene oxide with ammonia. Anhydrous or aqueous ammonia may be used, although anhydrous ammonia favors the production of monoalkanolamine, and may be used when the same is preferred. The resulting alkanolamines may be used, for example, in the treatment of natural gas. The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897.

The catalysts described in the following examples are prepared on supports having the following characteristics, shown in Table 1:

TABLE 1

Support Data

|  | A | B |
|---|---|---|
| Size (OD, in) | 0.32-0.36 | 0.32-0.36 |
| Surface Area (m2/g) | 1.28 | 1.03 |
| Pore Volume (ml/g) | 0.69 | 0.68 |
| Median Pore Diameter (microns) | 2.0 | 2.6 |
| <1 Micron Pores (%) | 11.5 | 6.0 |
| Crush Strength (lbs) | 21.4 | 19.6 |

EXAMPLE 1

Catalyst 1 (comparative) is prepared as described below with all the promoters being added during the second silver impregnation. A first impregnation of carrier A (10.30 g) is performed using roughly 30 mL of silver-amine-oxalate solution (26.6 wt % Ag) prepared as described under "Catalyst Preparation" in US 2009/177000 A1.

More specifically, the carrier is impregnated in an appropriately sized glass vessel which is equipped with stopcocks for impregnating the carrier under vacuum. A separatory funnel which is used for containing the impregnating solution is inserted through a rubber stopper into the top of the impregnating vessel. The impregnating vessel containing the carrier is evacuated to approximately 1-2" mercury absolute for 15 minutes, after which the impregnating solution is slowly added to the carrier by opening the stopcock between the separatory funnel and the impregnating vessel. After all the solution empties into the impregnating vessel (about 15 seconds), the vacuum is released and the pressure returned to atmospheric. Following addition of the solution, the carrier remains immersed in the impregnating solution at ambient conditions for 15 minutes, and is thereafter drained of excess solution for 15 minutes.

The silver-impregnated carrier is then roasted as follows to effect reduction of silver on the catalyst surface. The wet impregnated carrier pills are spread out in a monolayer on a stainless steel wire mesh with 3 mm apertures and placed on a nozzle connected to a hot air gun (Steinel HL1610S). The roasting procedure consisted of two stages. In the first stage the impregnated support was roasted at a temperature of 300° C. for 1.5 minutes with an air flow of 75 LPM/in$^2$; then in the second stage the temperature was increased to 400° C. for 2 minutes to complete the roasting. The air flow during the second roasting stage was 130 LPM/in$^2$. After completion of the roasting, the catalyst is cooled in open air to room temperature and weighed.

A second impregnation of the roasted catalyst pills is then performed using a solution prepared by adding the amounts of promoter solutions given in Table 1, below, to 40.7 g of silver-amine-oxalate solution composed of the drained solution from the first impregnation combined with fresh silver-amine-oxalate solution. The $Mn(NO_3)_2$ solution is complexed with $(NH_4)_2EDTA$ prior to its addition to silver-amine-oxalate solution. The impregnation, draining and roasting steps for this second impregnation are carried out analogously to the first impregnation. The composition of Catalyst 1 calculated based on silver uptake and amounts of added promoter solutions and after draining and roasting, is given in Table 2.

Catalyst 2 (inventive) is prepared with an identical target formulation as Catalyst 1, the only difference from Catalyst 1 being that the manganese promoter after complexation with $(NH_4)_2EDTA$ was added along with silver during the first Ag impregnation. All the other promoters were added during the second Ag impregnation. The final composition of Catalyst 2 calculated based on silver uptake and amounts of added promoter solutions is given in Table 2 below.

FIG. 1 above shows a comparison of the performance of Catalyst 1 and Catalyst 2 in the ethylene epoxidation reaction. The catalysts were tested in ¼ inch (outer diameter) stainless steel reactor tubes (once-through operation). An amount of 0.7 g of crushed catalysts (30/50 mesh sized) are thoroughly mixed with 1:1 by weight Denstone (inert from Norton Inc, USA) of the same particle size fraction and loaded in the reactor tubes. The feed compositions are: 30 mole-% ethylene, 8 mole-% oxygen, 1.5 mole-% carbon dioxide, 0.7 mole-% ethane and various ppmv levels of ethyl chloride. The total inlet gas flow rate is adjusted to give a gas hourly space velocity of 10000 h−1 as calculated for uncrushed catalyst. Reactor pressures are about 1950 KPa-gauge. The catalysts were operated at the same feed composition and a constant temperature of 240° C. Z* was varied by varying the ethyl chloride (ECL) concentration in the feed; the plot in FIG. 1 shows the change in outlet EO concentration and oxygen efficiency with variation in Z*. The maximum (peak) oxygen efficiency obtained with the inventive catalyst (Catalyst 2) is about 1% higher than that obtained with the comparative catalyst (Catalyst 1).

EXAMPLE 2

Catalyst 3 (inventive) was prepared with an identical target formulation as Catalyst 1, the only difference from Catalyst 1 being that the sodium promoter was added to the Ag solution during the first silver impregnation. All the other promoters were added during the second Ag impregnation. The amounts of promoter solutions added to the silver-amine-oxalate solution during the impregnation steps and the final calculated composition of the catalyst based on silver uptake and added promoter solutions is given in Table 2.

Figure 2:
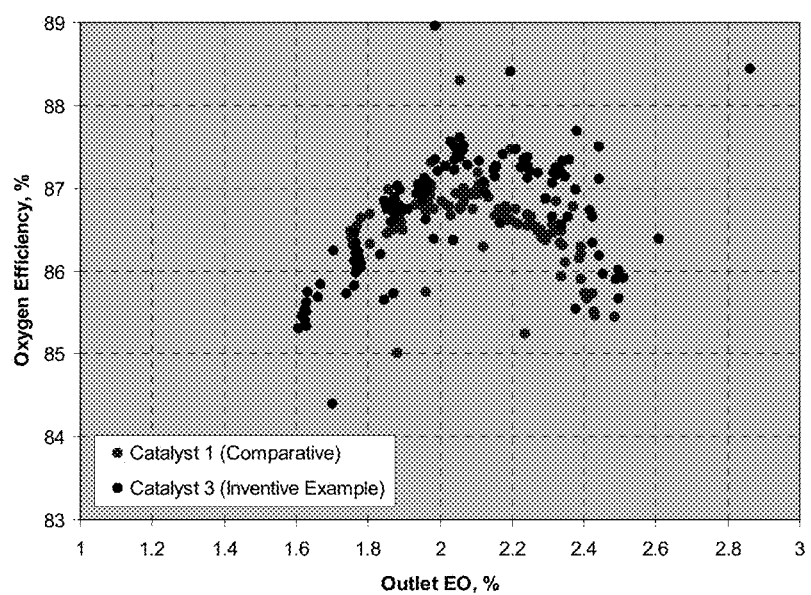
FIG. 2 is a graphical depiction of the % efficiency versus % outlet ethylene oxide concentration of a conventional epoxidation catalyst as well as an epoxidation catalyst produced according to one embodiment of the method.

FIG. 2 shows a comparison of the performance of Catalyst 1 and Catalyst 3 in the ethylene epoxidation reaction. The feed Z* was varied as described in Example 1 and the response is observed. The maximum oxygen efficiency obtained with the inventive catalyst (Catalyst 3) is 0.5-0.6% higher than that obtained with the comparative catalyst (Catalyst 1).

EXAMPLE 3

Catalyst 4 (comparative) was prepared with an identical target formulation as Catalyst 1, the only difference from Catalyst 1 being that the sodium promoter as well as the manganese promoter (complexed with $(NH_4)_2EDTA$) were added to the Ag solution during the first silver impregnation. The rest of the promoters were added to the silver-amine-oxalate solution during the second Ag impregnation. The amounts of promoter solutions added to the silver-amineoxalate solution during the impregnation steps and the final calculated composition of the catalyst based on silver uptake and added promoter solutions is given in Table 2.

Figure 3:
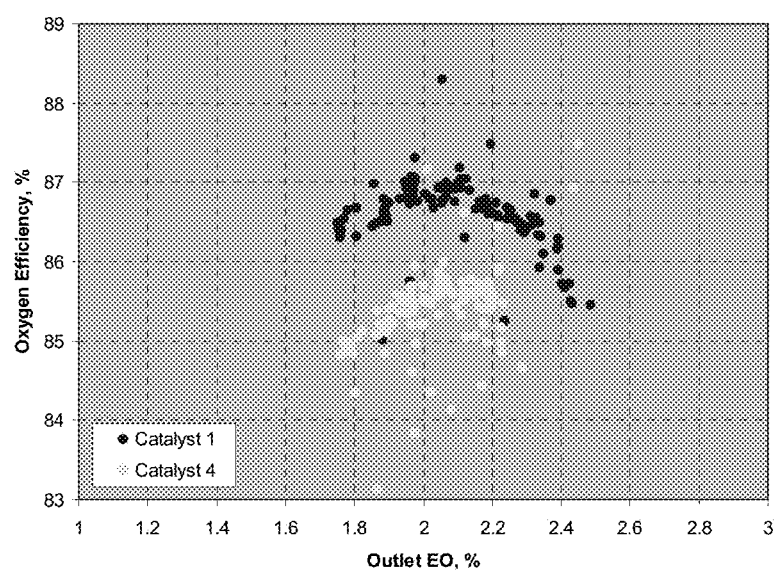
FIG. 3 is a graphical depiction of the % efficiency versus % outlet ethylene oxide concentration of a conventional epoxidation catalyst as well as an epoxidation catalyst produced according to one embodiment of the method.

FIG. 3 shows a comparison of the performance of Catalyst 1 and Catalyst 4 in the ethylene epoxidation reaction. The feed Z* was varied as described in Example 1 and the response is observed. The maximum oxygen efficiency obtained with Catalyst 4 is surprisingly 1.3% lower than that obtained for Catalyst 1.

Addition of either Mn or Na in the first Ag impregnation provides an improvement in the efficiency as illustrated in examples 1 and 2; however, as shown in example 3, addition of Mn and Na together in the first Ag impregnation is detrimental to efficiency.

EXAMPLE 4

Catalyst 5 (comparative) was prepared with all the promoters being added during the second silver impregnation The amounts of promoter solutions added to the silver-amine-oxalate solution during the second impregnation and the final composition of the catalyst calculated based on the silver uptake and amounts of promoter solutions added is given in Table 2.

Catalyst 6 (inventive) was prepared with an identical target formulation as Catalyst 5, the only difference from Catalyst 5 being that the sodium promoter was added to the Ag solution during the first silver impregnation. All the other promoters were added during the second Ag impregnation. The final calculated composition of catalyst 6 is given in Table 2.

Figure 4:
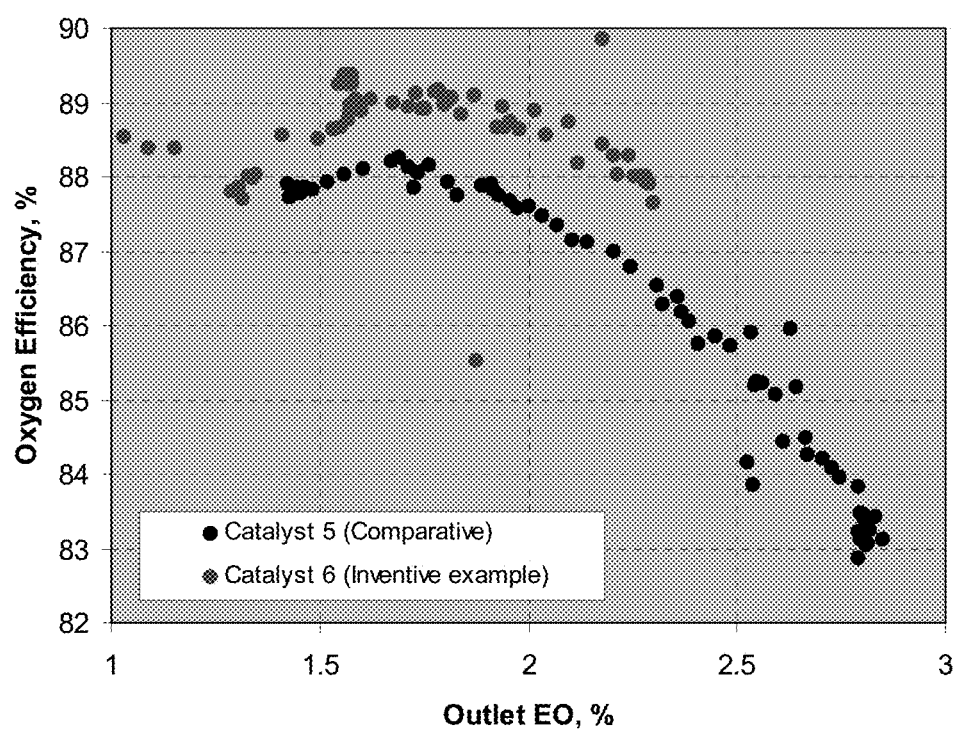
FIG. 4 is a graphical depiction of the % efficiency versus % outlet ethylene oxide concentration of a conventional epoxidation catalyst as well as an epoxidation catalyst produced according to one embodiment of the method.

FIG. 4 shows a comparison of the performance of Catalyst 5 and Catalyst 6 in the ethylene epoxidation reaction. The feed Z* was varied as described in Example 1 and the response is observed. The maximum oxygen efficiency obtained with the inventive catalyst (Catalyst 5) is 0.5-0.6% higher than that obtained with the comparative catalyst (Catalyst 5).

EXAMPLE 5

Catalyst 7 (inventive) was prepared with an identical target formulation as Catalyst 1, the only difference from Catalyst 1 being that the sodium and lithium promoters were added to the Ag solution during the first silver impregnation. The other promoters were added during the second Ag impregnation. The amounts of promoter solutions added to the silver-amine-oxalate solution during the impregnation steps and the final calculated composition of catalyst 7 based on silver uptake and added promoter solutions is given in Table 2.

Figure 5:
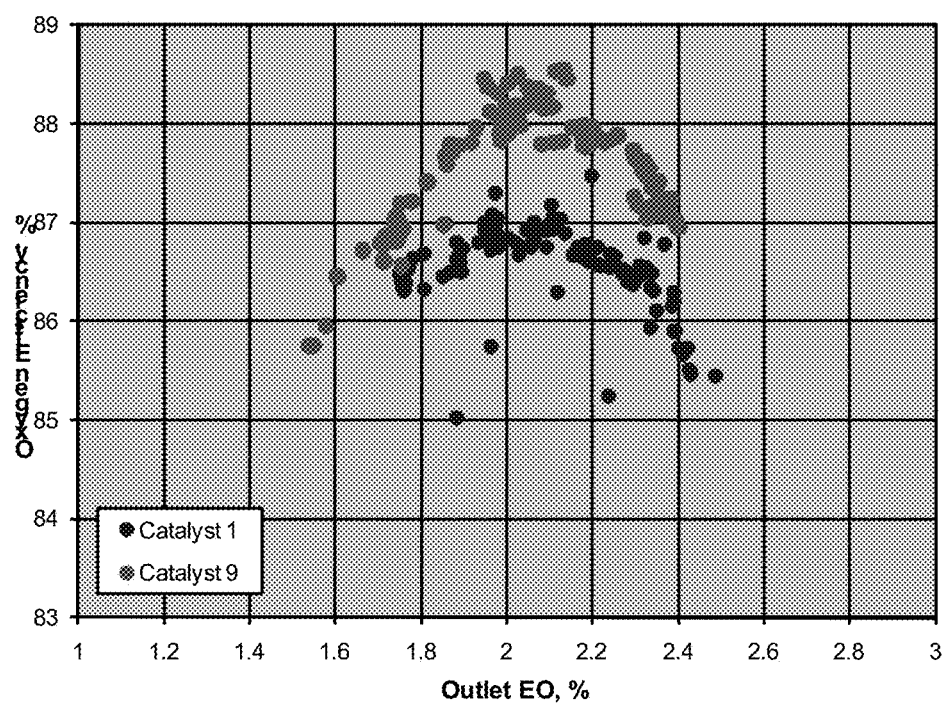
FIG. 5 is a graphical depiction of the % efficiency versus % outlet ethylene oxide concentration of a conventional epoxidation catalyst as well as an epoxidation catalyst produced according to one embodiment of the method.

FIG. 5 shows a comparison of the performance of Catalyst 1 and Catalyst 7 in the ethylene epoxidation reaction. The feed Z* was varied as described in Example 1 and the response is observed. The maximum oxygen efficiency obtained with Catalyst 7 is about 1.4% higher than that obtained for Catalyst 1.

Addition of Li and Na in the first Ag impregnation, with Mn being added in a separate second step provides an improvement in the efficiency as illustrated in examples 5. However, as shown in example 3, addition of Mn and Na together in the first Ag impregnation is detrimental to efficiency.

EXAMPLE 6

Catalyst 8 (inventive) is prepared with an identical target formulation as Catalyst 1, the only difference from Catalyst 1 being that the manganese promoter was added to the bare carrier prior to impregnation of the Ag solution. The catalyst preparation consisted of the following steps. A Mn solution was prepared by adding 0.0348 g of manganous nitrate solution (0.1552 g Mn/g solution) to 30 g of deionized water. 10.13 g of the carrier (Support No. A) was vacuum impregnated using the above solution. After draining the excess solution the carrier was roasted. A second vacuum impregnation was then performed using a silver-amine-oxalate solution containing 25.60 wt. % Ag. The weight of the catalyst after the Ag impregnation was 13.16 g, an Ag loading of 23.07%. Another impregnation of the roasted catalyst pills is then performed using a solution prepared by adding 0.0902 g of CsOH solution (0.4564 g Cs/g solution), 0.0944 g of lithium acetate solution (0.023 g Li/g solution), 0.0375 g of sodium acetate solution (0.071 g Na/g solution), 0.8042 g of ammonium perrhenate solution (0.0359 g Re/g solution), 0.0366 g of ammonium sulfate solution (0.2789 g $SO_4$/g solution), 0.0357 g of manganous nitrate solution (0.1552 g Mn/g solution) to 42.3 g of silver-amine-oxalate solution. The impregnation, draining and roasting steps for this impregnation step are carried out analogously to the earlier impregnations. After draining and roasting, the final catalyst weight was 15.79 g. The composition of Catalyst 8 calculated based on silver uptake and amounts of added promoter solutions was Ag: 35.71 wt %, Cs: 627 ppm, Li: 33 ppm, Na: 41 ppm, Re: 439 ppm, $SO_4$: 155 ppm, Mn: 82 ppm.

Figure 6:
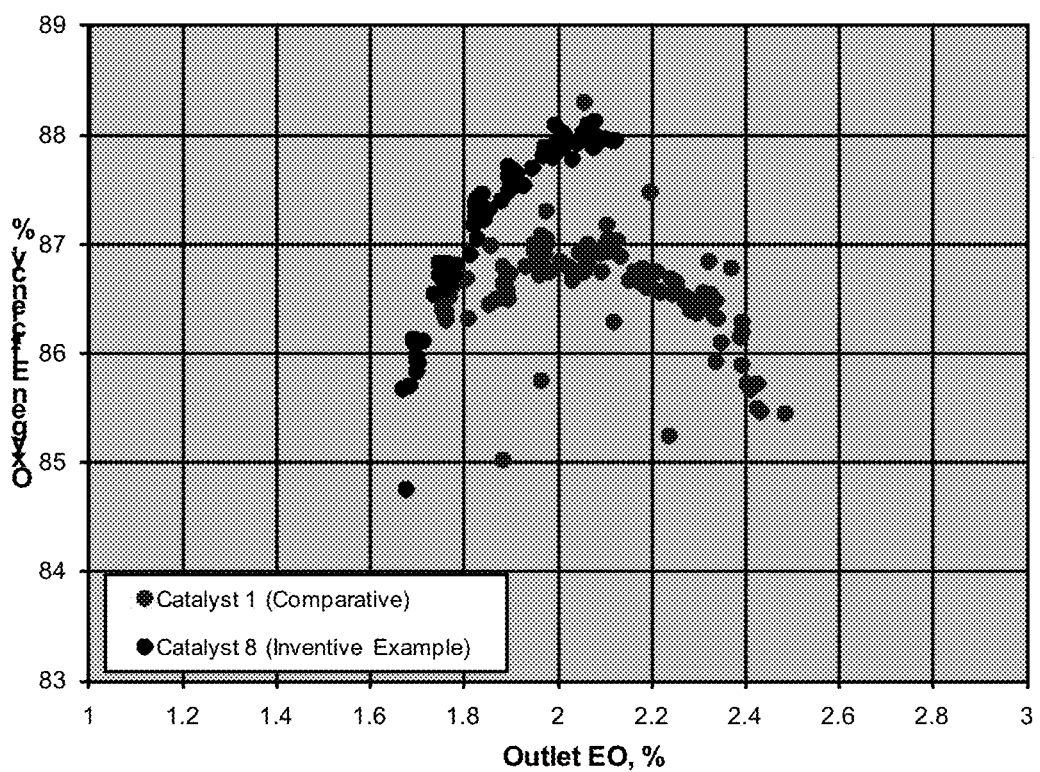
FIG. 6 is a graphical depiction of the % efficiency versus % outlet ethylene oxide concentration of a conventional epoxidation catalyst as well as an epoxidation catalyst produced according to one embodiment of the method.

FIG. 6 shows a comparison of the performance of Catalyst 1 and Catalyst 8 in the ethylene epoxidation reaction. The feed Z* was varied as described in Example 1 and the response is observed. The maximum oxygen efficiency obtained with Catalyst 8 is 1% higher than that obtained for Catalyst 1.

EXAMPLE 7

Catalyst 9 (comparative) was prepared with Ag impregnation being carried out only once. 10.34 g of carrier pills (Support No. A) was impregnated using a solution prepared by adding 0.0541 g of CsOH solution (0.4564 g Cs/g solution), 0.0605 g of lithium acetate solution (0.023 g Li/g solution), 0.0245 g of sodium acetate solution (0.071 g Na/g solution), 0.4823 g of ammonium perrhenate solution (0.0359 g Re/g solution), 0.0212 g of ammonium sulfate solution (0.2789 g $SO_4$/g solution), 0.0238 g of manganous nitrate solution (0.1552 g Mn/g solution) and 0.0947 g of diammonium EDTA solution (0.4128 g EDTA/g solution) to 42.0 g of silver-amine-oxalate solution containing 18.76 wt. % Ag. The impregnation, draining and roasting steps are carried out analogously to the earlier preparations. After draining and roasting, the final catalyst weight was 12.30 g. The composition of Catalyst 9 calculated based on silver uptake and amounts of added promoter solutions was Ag: 15.94 wt %, Cs: 499 ppm, Li: 28 ppm, Na: 35 ppm, Re: 350 ppm, $SO_4$: 120 ppm, Mn: 75 ppm.

Catalyst 10 (inventive) was prepared with an identical formulation as Catalyst 9, the only difference from Catalyst 9 being that the manganese promoter was added to the carrier before the impregnation of Ag and other promoters. The catalyst preparation consisted of the following steps. A Mn solution was prepared by adding 0.0334 g of manganous nitrate solution (0.1552 g Mn/g solution) to 30 g of deionized water. 10.26 g of the carrier (Support No. A) was vacuum impregnated using the above solution, the excess solution drained and the pills roasted. Subsequently another impregnation is carried out using a solution prepared by adding 0.0503 g of CsOH solution (0.4564 g Cs/g solution), 0.0560 g of lithium acetate solution (0.023 g Li/g solution), 0.0227 g of sodium acetate solution (0.071 g Na/g solution), 0.4477 g of ammonium perrhenate solution (0.0359 g Re/g solution), 0.0200 g of ammonium sulfate solution (0.2789 g $SO_4$/g solution) to 42.0 g of silver-amine-oxalate solution containing 18.76 wt. % Ag. The impregnation, draining and roasting steps are carried out analogously to the earlier preparations. After draining and roasting, the final catalyst weight was 12.23 g. The composition of Catalyst 10 calculated based on silver uptake and amounts of added promoter solutions was Ag: 16.13 wt %, Cs: 499 ppm, Li: 28 ppm, Na: 35 ppm, Re: 349 ppm, $SO_4$: 121 ppm, Mn: 113 ppm.

Figure 7:
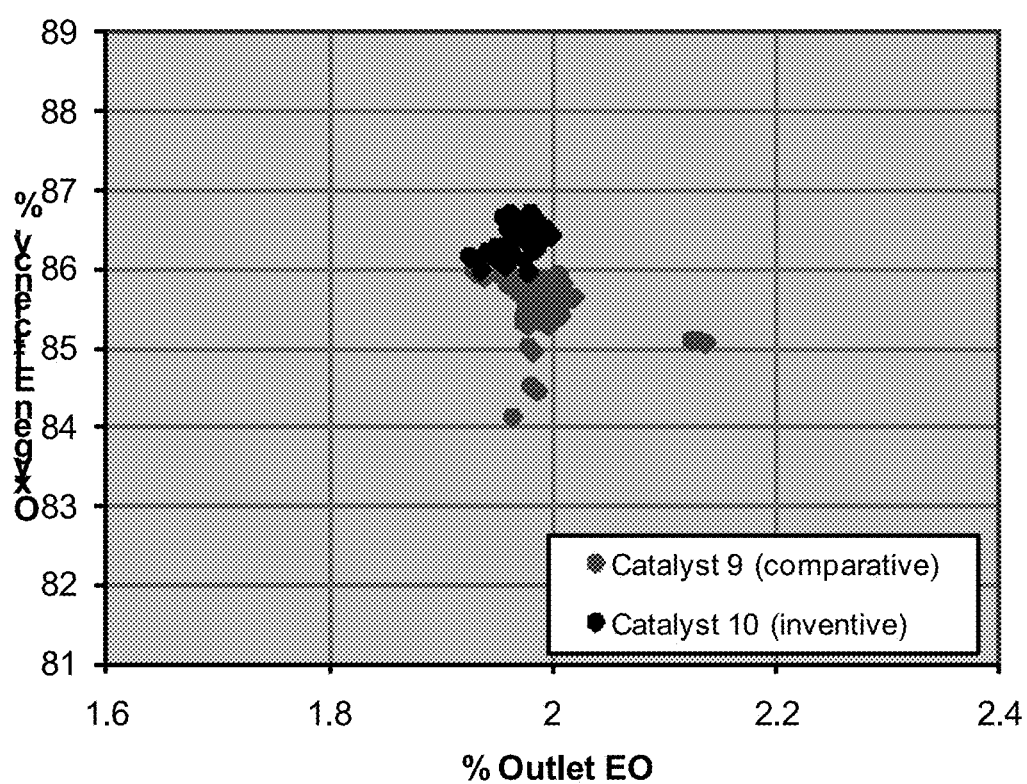
FIG. 7 is a graphical depiction of the % efficiency versus % outlet ethylene oxide concentration of a conventional epoxidation catalyst as well as an epoxidation catalyst produced according to one embodiment of the method.

FIG. 7 shows that the inventive example catalyst 10 provides 0.6-0.7% higher initial efficiency than the comparative catalyst 9.

TABLE 2

| | Catalyst number | | | | | | |
|---|---|---|---|---|---|---|---|
| | 1 | 2 | 3 | 4 | 5 | 6 | 7 |
| 1st Impregnation | | | | | | | |
| Support No. | A | A | A | A | B | B | A |
| Support (g) | 10.30 | 10.20 | 10.31 | 10.15 | 10.25 | 10.53 | 10.04 |
| Silver-Amine-Oxalate solution (g) | 40.1 | 43.5 | 43.3 | 43.6 | 42.6 | 41.3 | |
| Ag content of solution (Wt. %) | 26.6 | 26.6 | 26.6 | 26.6 | 26.6 | 26.6 | 26.55 |
| Promoter Soln. A, $Mn(NO_3)_2$ 0.1552 g Mn/g, (g) | | 0.0375 | | 0.0375 | | | |
| Chelating Agent, $(NH_4)_2$EDTA 0.4128 g EDTA/g, (g) | | 0.1474 | | 0.1475 | | | |
| Promoter Soln. B, $Na_2(O_2C_2H_3)$ 0.0710 g Na/g, (g) | | | 0.0440 | 0.0430 | | 0.0777 | 0.0405 |
| Promoter Soln. C, $Li_2(O_2C_2H_3)$ 0.0230 g Li/g, (g) | | | | | | | 0.1016 |
| Ag loading in 1st impregnation (Wt. %) | 20.20 | 20.66 | 20.55 | 22.13 | 20.87 | 20.01 | 22.60 |
| 2nd impregnation | | | | | | | |
| Weight of First dip catalyst (g) | 12.90 | 12.86 | 12.98 | 13.04 | 12.96 | 13.16 | |
| Silver-Amine_Oxalate solution (g) | 40.7 | 43.5 | 43.5 | 43.6 | 42.1 | 41.3 | |
| Promoter Soln. A, $Mn(NO_3)_2$ 0.1552 g Mn/g, (g) | 0.0357 | | 0.0374 | | 0.0682 | 0.0698 | 0.0358 |
| Chelating Agent, $(NH_4)_2$EDTA 0.4128 g EDTA/g, (g) | 0.1402 | | 0.1479 | | 0.2697 | 0.2734 | 0.1411 |
| Promoter Soln. B, $Na_2(O_2C_2H_3)$ 0.0710 g Na/g, (g) | 0.0412 | 0.0428 | | | 0.0836 | | ] |
| Promoter Soln. C, $Li_2(O_2C_2H_3)$ 0.0230 g Li/g, (g) | 0.1021 | 0.1069 | 0.1076 | 0.1013 | 0.2073 | 0.2104 | |
| Promoter soln. D, CsOH 0.4564 g Cs/g, (g) | 0.0982 | 0.1028 | 0.1032 | 0.0974 | 0.1616 | 0.1649 | 0.0986 |

TABLE 2-continued

| | Catalyst number | | | | | | |
|---|---|---|---|---|---|---|---|
| | 1 | 2 | 3 | 4 | 5 | 6 | 7 |
| Promoter soln. E, NH$_4$ReO$_4$ 0.0359 g Re/g (g) | 0.8744 | 0.9174 | 0.9210 | 0.8683 | 1.4412 | 1.4642 | 0.8780 |
| Promoter soln. F, (NH$_4$)$_2$SO$_4$ 0.2789 g SO$_4$/g (g) | 0.0399 | 0.0418 | 0.0419 | 0.0396 | 0.0656 | 0.0670 | 0.0401 |
| Final Catalyst Weight (g) | 15.31 | 15.22 | 15.48 | 15.39 | 15.56 | 15.7 | 15.76 |
| Ag content (Wt. %) | 32.58 | 32.84 | 33.22 | 33.88 | 33.86 | 32.67 | 36.13 |
| Final Promoter Levels | | | | | | | |
| Promoter A, Mn (ppm) | 80 | 77 | 80 | 86 | 156 | 157 | 85 |
| Promoter B, Na (ppm) | 42 | 40 | 43 | 45 | 87 | 80 | 44 |
| Promoter C, Li (ppm) | 34 | 33 | 34 | 30 | 70 | 70 | 36 |
| Promoter D, Cs (ppm) | 644 | 624 | 651 | 580 | 1086 | 1088 | 691 |
| Promoter E, Re (ppm) | 451 | 438 | 457 | 406 | 762 | 760 | 484 |
| Promoter F, SO$_4$ (ppm) | 160 | 155 | 161 | 144 | 269 | 269 | 172 |

The data presented demonstrate that the selection of promoters to be added in the first Ag impregnation is not trivial. Selection of promoters that need to added together in the same step, and promoters that should not be mixed together and be added in separate steps is also not trivial.

We claim:

1. A method for the epoxidation of one or more alkylenes comprising contacting one or more feed streams comprising an oxygen source and an alkylene in the presence of an epoxidation catalyst, wherein the epoxidation catalyst comprises a support, silver, manganese and greater than 35 ppm sodium, and is prepared by a method comprising:
   Impregnating the support with manganese prior to impregnating the support with sodium; and
   Impregnating the support with silver prior to, at the same time as or after impregnation with manganese.

2. The method of claim 1, carried out in the gas phase over a packed catalyst bed wherein the gas hourly space velocity in the start-up phase is from 2000 to 10000 per hour.

3. The method of claim 1, wherein the alkylene comprises 1,9-decadiene, 1,3-butadiene, 2-butene, isobutene, 1-butene, propylene, ethylene, or combinations of these.

4. The method of claim 1, wherein the one or more feed streams further comprises one or more gas phase promoters selected from the group consisting of methyl chloride, ethyl chloride, ethylene dichloride, ethylene dibromide, vinyl chloride, and any combination of these.

5. The method of claim 1, wherein the one or more feed streams further comprises carbon dioxide in a concentration of at most 3 mole percent, based on the total reaction mixture.

6. The method of claim 1, wherein the concentration of oxygen within the oxygen source is decreased by up to 3 mole percent during the epoxidation process.

7. The method of claim 5, wherein the concentration of carbon dioxide is increased during the epoxidation process by at least 0.5 mole percent during the epoxidation process.

8. A method for the epoxidation of one or more alkylenes comprising contacting one or more feed streams comprising an oxygen source and an alkylene in the presence of an epoxidation catalyst, wherein the epoxidation catalyst comprises a support, silver, manganese and greater than 35 ppm sodium, and is prepared by a method comprising:
   Impregnating the support with manganese separately from sodium and exposing the catalyst in between impregnations to an elevated temperature not exceeding 600° C.

9. The method of claim 8, carried out in the gas phase over a packed catalyst bed wherein the gas hourly space velocity in the start-up phase is from 2000 to 10000 per hour.

10. The method of claim 8, wherein the alkylene comprises 1,9-decadiene, 1,3-butadiene, 2-butene, isobutene, 1-butene, propylene, ethylene, or combinations of these.

11. The method of claim 8, wherein the one or more feed streams further comprises one or more gas phase promoters selected from the group consisting of methyl chloride, ethyl chloride, ethylene dichloride, ethylene dibromide, vinyl chloride, and any combination of these.

12. The method of claim 8, wherein the one or more feed streams further comprises carbon dioxide in a concentration of at most 3 mole percent, based on the total reaction mixture.

13. The method of claim 12, wherein the concentration of carbon dioxide is increased during the epoxidation process by at least 0.5 mole percent during the epoxidation process.

14. The method of claim 1, further comprising reacting the alkylene oxide with water, alcohol, ammonia and/or carbon dioxide to provide a 1,2-diol, 1,2-diol ether, a 1,2-carbonate, or alkanolamine.

15. The method of claim 14, wherein the alkylene oxide is reacted with water and/or alcohol, optionally in the presence of an acidic or basic catalyst, to produce one or more 1,2-diols or 1,2-diol ethers.

16. The method of claim 14, wherein the alkylene oxide is reacted with ammonia to produce one or more alkanolamines.

17. The method of claim 14, wherein the the alkylene oxide is reacted with carbon dioxide to provide a 1,2-carbonate.

18. The method of claim 8, further comprising reacting the alkylene oxide with water, alcohol, ammonia and/or carbon dioxide to provide a 1,2-diol, 1,2-diol ether, a 1,2-carbonate, or alkanolamine.

19. The method of claim 18, wherein the alkylene oxide is reacted with water and/or alcohol, optionally in the presence of an acidic or basic catalyst, to produce one or more 1,2-diols or 1,2-diol ethers.

20. The method of claim 18, wherein the alkylene oxide is reacted with ammonia to produce one or more alkanolamines, or, reacting the alkylene oxide with carbon dioxide to provide a 1,2-carbonate.

\* \* \* \* \*